(12) United States Patent
Abunassar et al.

(10) Patent No.: US 12,138,169 B2
(45) Date of Patent: Nov. 12, 2024

(54) FIXATION DEVICE HAVING A FLEXURE PORTION

(71) Applicant: EVALVE, INC., Santa Clara, CA (US)

(72) Inventors: Chad Abunassar, San Francisco, CA (US); Gabriel Gonzales, Milpitas, CA (US); Samir Jain, Mountain View, CA (US); Jill McCoy, Los Altos, CA (US)

(73) Assignee: EVALVE, INC., Santa Clara, CA (US)

( * ) Notice: Subject to any disclaimer, the term of this patent is extended or adjusted under 35 U.S.C. 154(b) by 345 days.

(21) Appl. No.: 17/732,830

(22) Filed: Apr. 29, 2022

(65) Prior Publication Data
US 2022/0346954 A1    Nov. 3, 2022

Related U.S. Application Data

(60) Provisional application No. 63/182,167, filed on Apr. 30, 2021.

(51) Int. Cl.
*A61F 2/24*    (2006.01)

(52) U.S. Cl.
CPC .... *A61F 2/2466* (2013.01); *A61F 2220/0016* (2013.01); *A61F 2230/0026* (2013.01)

(58) Field of Classification Search
CPC .... A61F 2/246; A61F 2/2466; A61B 17/1227; A61B 17/1285
See application file for complete search history.

(56) References Cited

U.S. PATENT DOCUMENTS

| 3,378,010 A | 4/1968 | Codling et al. |
| 3,874,388 A | 4/1975 | King et al. |

(Continued)

FOREIGN PATENT DOCUMENTS

| CA | 2 296 317 C | 1/2009 |
| CN | 106102599 | 11/2016 |

(Continued)

OTHER PUBLICATIONS

Extended European Search Report dated Aug. 29, 2022 in Application No. EP 22170956.

(Continued)

*Primary Examiner* — Brian A Dukert
(74) *Attorney, Agent, or Firm* — SLEMAN & LUND LLP

(57) ABSTRACT

Fixation device for fixation of leaflets of a heart valve, the fixation device including a central element defining a central axis. The fixation device further includes a distal portion including at least one arm coupled to the central element, wherein the at least one arm is moveable to a selected position between a fully open position and a fully closed position. The distal portion further includes at least one leg operatively coupled to the at least one arm and configured to move the at least one arm to the selected position between the fully open position and the fully closed position. The at least one arm includes a contact portion configured to engage native heart valve tissue, the contact portion defining a contact portion axis. The distal portion includes a flexure portion configured to enable the contact portion in the selected position to move within a flex angle range between an undeformed contact portion angle relative to the central axis and a flexed contact portion angle relative to the central axis. The flexed contact portion angle is greater than the undeformed contact portion angle. The flex angle range is about 10 degrees to about 45 degrees. The fixation device further includes at least one gripping element moveable relative to the at least one arm to capture a native leaflet therebetween.

25 Claims, 14 Drawing Sheets

(56) References Cited

U.S. PATENT DOCUMENTS

| | | |
|---|---|---|
| 4,007,743 A | 2/1977 | Blake |
| 4,055,861 A | 11/1977 | Carpentier et al. |
| 4,327,736 A | 5/1982 | Inoue |
| 4,340,091 A | 7/1982 | Skelton et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 5,002,562 A | 3/1991 | Oberlander |
| 5,069,679 A | 12/1991 | Taheri |
| 5,098,440 A | 3/1992 | Hillstead |
| 5,125,895 A | 6/1992 | Buchbinder et al. |
| 5,147,370 A | 9/1992 | McNamara et al. |
| 5,171,259 A | 12/1992 | Inoue |
| 5,222,963 A | 6/1993 | Brinkerhoff et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,843,178 A | 12/1998 | Vanney et al. |
| 5,849,019 A | 12/1998 | Yoon |
| 5,855,601 A | 1/1999 | Bessler et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,346,074 B1 | 2/2002 | Roth |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 7,011,669 B2 | 3/2006 | Kimblad |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,556,632 B2 | 7/2009 | Zadno |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,972,323 B1 | 7/2011 | Bencini et al. |
| 7,981,139 B2 | 7/2011 | Martin et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 9,510,829 B2 | 12/2016 | Goldfarb et al. |
| 10,076,415 B1 | 9/2018 | Metchik et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 | 3/2019 | Metchik et al. |
| 10,238,493 B1 | 3/2019 | Metchik et al. |
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 11,464,636 B2 | 10/2022 | Abunassar |
| 11,660,189 B2 | 5/2023 | Abunassar |
| 2002/0013571 A1 | 1/2002 | Goldfarb et al. |
| 2002/0183787 A1 | 12/2002 | Wahr et al. |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2005/0267493 A1 | 12/2005 | Schreck et al. |
| 2006/0020275 A1 | 1/2006 | Goldfarb et al. |
| 2006/0089671 A1 | 4/2006 | Goldfarb |
| 2007/0038293 A1 | 2/2007 | St.Goar et al. |
| 2011/0004227 A1 | 1/2011 | Goldfarb |
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |

(56) References Cited

U.S. PATENT DOCUMENTS

| | | |
|---|---|---|
| 2018/0092661 A1 | 4/2018 | Prabhu |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0296329 A1 | 10/2018 | Dixon et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0083251 A1 | 3/2019 | Hariton et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0175182 A1 | 6/2019 | Goldfarb |
| 2019/0183571 A1 | 6/2019 | De Marchena |
| 2019/0209293 A1 | 7/2019 | Metchik et al. |
| 2019/0209297 A1 | 7/2019 | Metchik |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |
| 2021/0015614 A1 | 1/2021 | Kizuka |
| 2021/0106419 A1 | 4/2021 | Abunassar |
| 2021/0145574 A1 | 5/2021 | Childs |
| 2021/0186698 A1 | 6/2021 | Abunassar |

FOREIGN PATENT DOCUMENTS

| | | |
|---|---|---|
| CN | 207368927 | 5/2018 |
| CN | 114176837 A | 3/2022 |
| CN | 216221859 U | 4/2022 |
| CN | 115300181 A | 11/2022 |
| EP | 0 558 031 B1 | 9/1993 |
| EP | 1383448 B1 | 6/2008 |
| FR | 2 768 324 A1 | 3/1999 |
| FR | 2 768 325 B1 | 11/1999 |
| JP | 2008517732 A | 5/2008 |
| JP | 6 732663 B2 | 7/2020 |
| WO | WO 91/01689 A1 | 2/1991 |
| WO | WO 92/12690 A1 | 8/1992 |
| WO | WO 94/18893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | WO 2016/099650 A1 | 6/2016 |
| WO | WO 2016/178722 A1 | 11/2016 |
| WO | WO 2018/093663 A1 | 5/2018 |
| WO | 2019129024 | 7/2019 |
| WO | 2021011531 A1 | 1/2021 |
| WO | WO 2021/027588 A1 | 2/2021 |

OTHER PUBLICATIONS

U.S. Appl. No. 62/874,280, filed Jul. 15, 2019, Childs.
U.S. Appl. No. 62/874,342, filed Jul. 15, 2019, Abunassar et al.
U.S. Appl. No. 62/914,211, filed Oct. 11, 2019, Abunassar.
U.S. Appl. No. 62/930,948, filed Nov. 5, 2019, Kizuka.
U.S. Appl. No. 62/949,563, filed Dec. 18, 2019, Abunassar et al.

FIXATION DEVICE HAVING A FLEXURE PORTION

CROSS-REFERENCE TO RELATED APPLICATIONS

This application claims priority to U.S. Provisional Application Ser. No. 63/182,167, filed on Apr. 30, 2021, which is incorporated by reference herein in its entirety.

FIELD OF DISCLOSED SUBJECT MATTER

The disclosed subject matter is directed to medical devices for the endovascular, percutaneous, or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

DESCRIPTION OF RELATED ART

Treatments for mitral valve regurgitation rely on valve replacement or repair including leaflet and annulus remodeling, the latter generally referred to as valve annuloplasty. Another technique for mitral valve repair, which relies on suturing adjacent segments of opposed valve leaflets together is referred to as the "edge-to-edge" or "bow-tie" technique. The edge-to-edge technique can be performed via open chest access, but an endovascular approach is preferable. An endovascular approach can include an endovascular system wherein a catheter is advanced to the heart from a remote vasculature location. Furthermore, such endovascular system should allow for repositioning and optional removal of a fixation device (i.e., valve repair clip) prior to fixation to ensure optimal placement. Such endovascular system likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a fixation device for fixation of leaflets of a heart valve includes a central element defining a central axis. The fixation device further includes a distal portion including at least one arm coupled to the central element, wherein the at least one arm is moveable to a selected position between a fully open position and a fully closed position. The distal portion further includes at least one leg operatively coupled to the at least one arm and configured to move the at least one arm to the selected position between the fully open position and the fully closed position. The at least one arm includes a contact portion configured to engage native heart valve tissue, the contact portion defining a contact portion axis. Additionally, the distal portion includes a flexure portion configured to enable the contact portion in the selected position to move within a flex angle range between an undeformed contact portion angle relative to the central axis and a flexed contact portion angle relative to the central axis. The flexed contact portion angle is greater than the undeformed contact portion angle. Further, the flex angle range is about 5 degrees to about 30 degrees. The fixation device also includes at least one gripping element moveable relative to the at least one arm to capture a native leaflet therebetween.

In accordance with the disclosed subject matter, the at least one arm can include the flexure portion. The at least one arm can also include a deformable frame comprising the flexure portion and having first and second deformable portions. Each of the first and second deformable portions can be disposed along a respective lateral side of the deformable frame. Furthermore, each of the first and second deformable portions can have an undeformed condition wherein the contact portion is at the undeformed contact portion angle and a deformed condition wherein the contact portion is at the flexed contact portion angle. The flexure portion can include at least one slit configured to enable the contact portion to move between the undeformed contact portion angle and the flexed contact portion angle.

Furthermore, the at least one slit can include at least one transverse cut in opposing lateral sides of the at least one arm. Further, the at least one slit can include a plurality of transverse cuts extending from each opposing lateral side of the at least one arm. Each of the at least one slit can be between about 0.01 inch to about 0.03 inch wide. Additionally, each of the at least one slit can be filled with a polymer having a durometer less than a durometer of the at least one arm. Furthermore, the at least one slit can be formed of a kerf cut. The at least one arm can extend from a first end proximate the central element to an opposing second end, wherein the contact portion can be proximate the opposing second end, and the flexure portion can be adjacent the contact portion. Additionally, the at least one gripping element can include a mid-length portion disposed along the at least one gripping element and spaced from a free end of the at least one gripping element. The at least one gripping element can further include an end portion proximate the free end. The end portion can be biased towards the at least one arm relative to the mid-length portion.

In accordance with another aspect of the disclosed subject matter, the at least one leg can include the flexure portion. The flexure portion can include a spring feature configured to deform elastically under a compressive load. The flexure portion can include a C-shaped compression link configured to enable the flex angle range be up to about 15 degrees. The flexure portion can include an S-shaped compression link configured to enable the flex angle range be up to about 30 degrees. The flexure portion can further include a trapezoidal-shaped compression link configured to enable the flex angle range be up to about 10 degrees. The trapezoidal-shaped compression link can have a width dimension that increases from a proximal location to a distal location. Further, the flexure portion can include at least one stop configured to limit the flex angle range. The stop can limit the flex angle range to up to about 10 degrees and be applied to any of the described aspects or embodiments. The flexure portion can include an arm flexure portion disposed on the at least one arm configured to enable an arm source flexion range. The flexure portion can further include a leg flexure portion disposed on the at least one leg configured to enable a leg source flexion range. The arm source flexion range and leg source flexion range can combine to enable the flex angle range. The combined arm source flex angle range and leg source flex angle range can be about 45 degrees or less.

Additionally, the central element can include a base portion coupled to the at least one leg, wherein distal movement of the base portion can move the at least one leg to move the at least one arm towards the fully open position. In this manner, the fixation device can be configured to prevent distal movement of the base portion when the at least one arm is in the selected position. The fixation device can further include a locking mechanism configured to prevent distal movement of the base portion.

DETAILED DESCRIPTION

Figure 1:
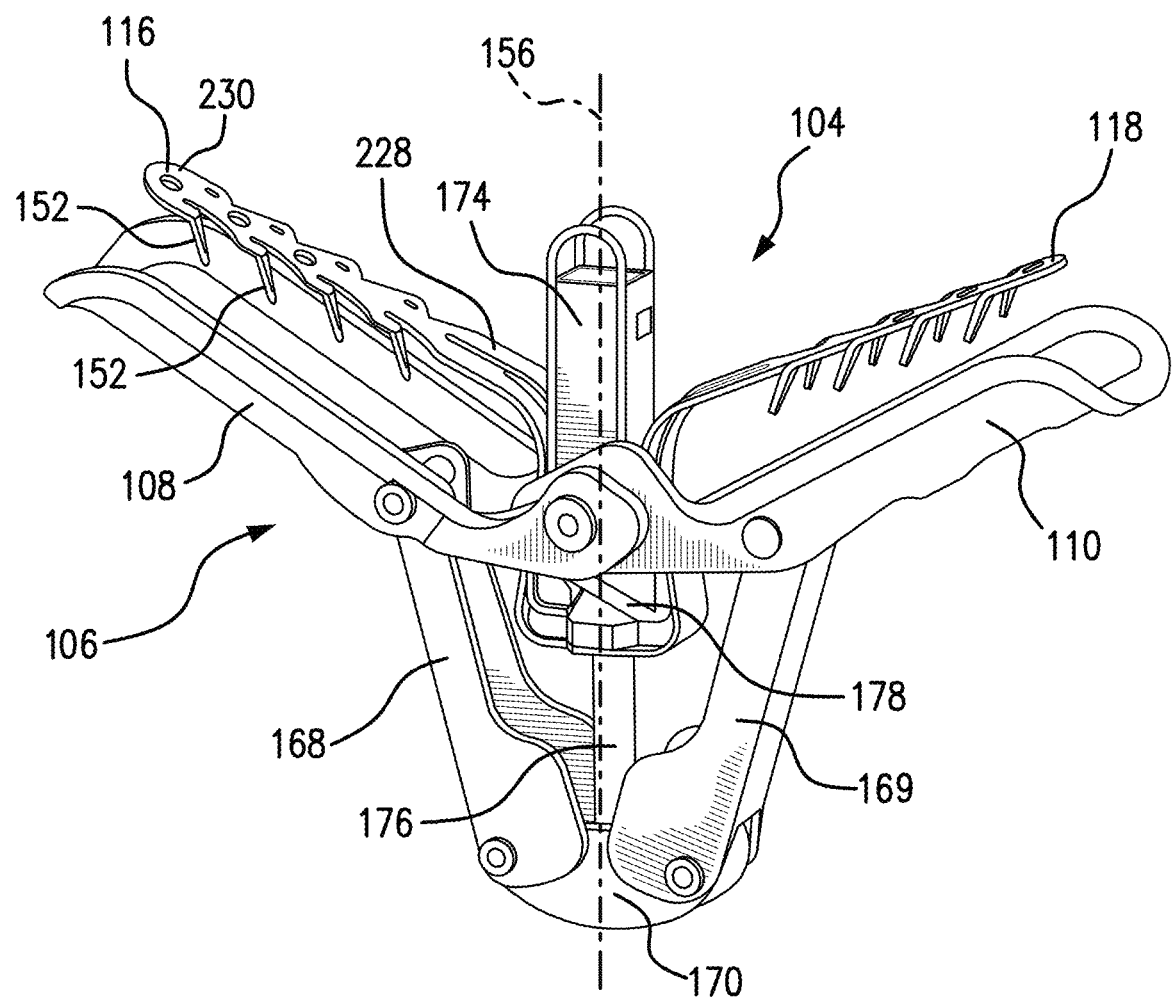
FIG. 1 is a perspective view of an exemplary embodiment of a fixation device for use in accordance with the disclosed subject matter.

Reference will now be made in detail to the various exemplary embodiments of the disclosed subject matter, exemplary embodiments of which are illustrated in the accompanying drawings.

The fixation device for use with the disclosed subject matter provides an edge-to-edge transcatheter valve repair option for patients having various conditions, including regurgitant mitral valves or tricuspid valves. Transcatheter (e.g., trans-septal) edge-to-edge valve repair has been established using a fixation device, such as the MitraClip Transcatheter Mitral Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (e.g., a proximal element) can be lowered or moved toward the arm and into contact with the atrial side of the native leaflet to capture the leaflet therebetween. Once each native leaflet is captured by a respective arm and gripping element, the fixation device can be closed by raising or moving the arms toward a center of the fixation device such that the leaflets are brought into coaptation, which results in a reduction in valvular regurgitation during ventricular systole. Furthermore, a covering can be provided on the arms and/or gripping elements to facilitate tissue ingrowth with the captured leaflets.

Additional details of exemplary fixation devices in accordance with the disclosed subject matter are set forth below. Furthermore, a number of patents and publications disclose additional details and aspects of such fixation devices and related operations. See for example, U.S. Pat. No. 7,226,467 to Lucatero et al.; U.S. Pat. No. 7,563,267 to Goldfarb et al.; U.S. Pat. No. 7,655,015 to Goldfarb et al.; U.S. Pat. No.

7,736,388 to Goldfarb et al.; U.S. Pat. No. 7,811,296 to Goldfarb et al.; U.S. Pat. No. 8,057,493 to Goldfarb et al.; U.S. Pat. No. 8,303,608 to Goldfarb et al.; U.S. Pat. No. 8,500,761 to Goldfarb et al.; U.S. Pat. No. 8,734,505 to Goldfarb et al.; U.S. Pat. No. 8,740,920 to Goldfarb et al.; U.S. Pat. No. 9,510,829 to Goldfarb et al.; U.S. Pat. No. 7,635,329 to Goldfarb et al.; U.S. Patent Application Publication No. 2017/0042546 to Goldfarb et al.; U.S. Patent Application Publication No. 2017/0239048 to Goldfarb et al.; U.S. Patent Application Publication No. 2018/0325671 to Abunassar et al.; U.S. Provisional Patent Application No. 62/874,342, filed Jul. 15, 2019; U.S. Provisional Patent Application No. 62/874,280, filed Jul. 15, 2019; U.S. Provisional Patent Application No. 62/930,948, filed Nov. 5, 2019; U.S. Provisional Patent Application No. 62/914,211, filed Oct. 11, 2019; and U.S. Provisional Patent Application No. 62/949,563, filed Dec. 18, 2019, the entirety of the contents of each of these patents and published applications is incorporated herein by reference.

In grasping tissue and leaflet capture for mitral valve disease, certain patient conditions and anatomies, such as those associated with larger dynamic gaps between leaflet tips, can create challenges for capture. As such, there is an opportunity for a fixation device capable of more reliable leaflet grasping, for example in cases of dynamic, chaotic, or overly severe degenerative mitral regurgitation (DMR), such as in cases of Barlow's Syndrome. When capturing leaflets, and particularity with leaflets having challenging anatomical features, a fixation device can pull tissue into a state of tension that can cause uneven stress on the leaflet.

In some cases, the uneven stress can occur at particular locations on the leaflet. For example, leaflet stress can be unevenly large proximate certain locations on the arms of the fixation device, such as near contact portions. Contact portions can be defined at any area along the arms. For example, contact portions can be defined along the majority of the length of the arms. Alternatively, the contact portion can be smaller, for example, at only an outer half or outer quarter of the length of the arms, where grasped tissue bends around outer edges of the arms. When tissue bends around the arms, the bends can form a small radius of curvature concentrating tissue stress and strain in that location. Additionally, increased tissue stress can also be a result of leaflets having different thicknesses wherein stress concentrations can be excessive in one leaflet and insufficient in another leaflet. Furthermore, tissue stress can also be uneven at certain times, such as during a portion of a cycle of heart contraction and when a user is maneuvering the position of the fixation device.

To reduce uneven leaflet tension and stress, contact portions on the arms can be configured to flex. The contact portion of the arm configured to flex can be the entire arm. Alternatively, the contact portion configured to flex can be only an outer half or outer quarter of the length of the arm. Thus, tissue can be grasped in both a non-flexible inner portion of the arm and a more flexible outer portion of the arm. The ability to flex of the contact portions can be relative to other portions of the arm and also relative to the remainder of the fixation device. As such, contact portions on different arms can flex independent of each other, which can be beneficial when treating leaflets having different thicknesses, and can have the added benefit of allowing a user to visualize an uneven grasp between multiple leaflets. Furthermore, a fixation device can be configured with an arm having a contact portion that is enabled to flex a different amount than another arm and contact portion on the same device. Allowing additional flex on one side of fixation device is to reduce leaflet stress interprocedurally when grasping leaflets independently. For example, a leaflet can be grasped first with the flexible side, and then the fixation device can be moved and oriented to capture a leaflet with the other non-flexible side.

Generally, and as set forth in greater detail below, the disclosed subject matter provided herein includes a fixation device for fixation of leaflets of a heart valve, wherein the fixation includes a central element defining a central axis. The fixation device further includes a distal portion including at least one arm coupled to the central element, wherein the at least one arm is moveable to a selected position between a fully open position and a fully closed position. The distal portion further includes at least one leg operatively coupled to the at least one arm and configured to move the at least one arm to the selected position between the fully open position and the fully closed position. The at least one arm includes a contact portion configured to engage native heart valve tissue, the contact portion defining a contact portion axis. Further, the distal portion includes a flexure portion configured to enable the contact portion in the selected position to move within a flex angle range between an undeformed contact portion angle relative to the central axis and a flexed contact portion angle relative to the central axis. Additionally, the flexed contact portion angle is greater than the undeformed contact portion angle. The flex angle range is about 5 degrees to about 30 degrees. The fixation device further includes at least one gripping element moveable relative to the at least one arm to capture a native leaflet therebetween.

Referring to FIGS. 1-2 for the purpose of illustration and not limitation, a fixation device 104 for fixation of native leaflets of a heart valve is disclosed herein. The fixation device 104 as embodied herein includes a central element 174 defining a central axis 156. The central element 174 can include various central components for operation and release of the fixation device. The fixation device 104 further includes a distal portion 106 including at least one arm 108, 110 coupled to the central element 174, wherein the at least one arm 108, 110 is moveable to a selected position between a fully open position and a fully closed position. For purpose of understanding and reference only, FIGS. 1-2 depict a fixation device without the flexure portions 150 of the disclosed subject matter.

With reference to FIG. 2, for illustration and not limitation, each arm 108, 110 can be rotatable or moved about a respective axis point between closed, open, and inverted positions, as well as any position therebetween. Furthermore, the arms 108, 110 can be selected from a range of suitable lengths, wherein the appropriate length can be selected by the physician or health care provider after inspection of a patient. For purpose of comparison, a first length of each arm 108, 110 is depicted in FIG. 2 in solid lines, and a second longer length of each arm of the disclosed subject matter is depicted in dashed lines. Each arm depicted in solid lines can be an entirely separate arm with a different length as compared to the corresponding arm depicted in dashed lines.

For example, and not limitation, and with reference to FIG. 1, the distal portion 106 further includes at least one leg 168, 169 operatively coupled to the at least one arm 108, 110 and configured to move the at least one arm 108, 110 to the selected position between the fully open position and the fully closed position. Additionally, the central element 174 can include a base portion 170 coupled to the at least one leg 168, 169, wherein distal movement of the base portion 170 can move the at least one leg 168, 169 to move the at least one arm 108, 110 towards the fully open position. In this manner, the fixation device 104 can be configured to prevent distal movement of the base portion 170 when the at least one arm 108, 110 is in the selected position. Furthermore, the base portion 170 can be operatively connected with a stud 176 which can be operatively attached to a distal end of a delivery shaft (not shown for clarity). In some embodiments, the stud 176 can be threaded so that the distal end of a delivery shaft can attach to the stud 176 by a screw-type action. Further, the connection point between the stud 176 and the distal end of a delivery shaft can be disposed within the central element 174. However, the distal end of a delivery shaft and stud 176 can be operatively connected by any mechanism which is releasable to allow the fixation device 104 to be detached. The stud can be axially extendable and retractable to move the base and therefore the legs 168, 169 which pivot the arms 108, 110 between closed, open, and inverted positions. The fixation device 104 can further include a locking mechanism 178 configured to prevent distal movement of the base portion 170. The locking mechanism can immobilize the stud. Further details are disclosed in the patents and publications incorporated by reference herein.

Figure 2A:
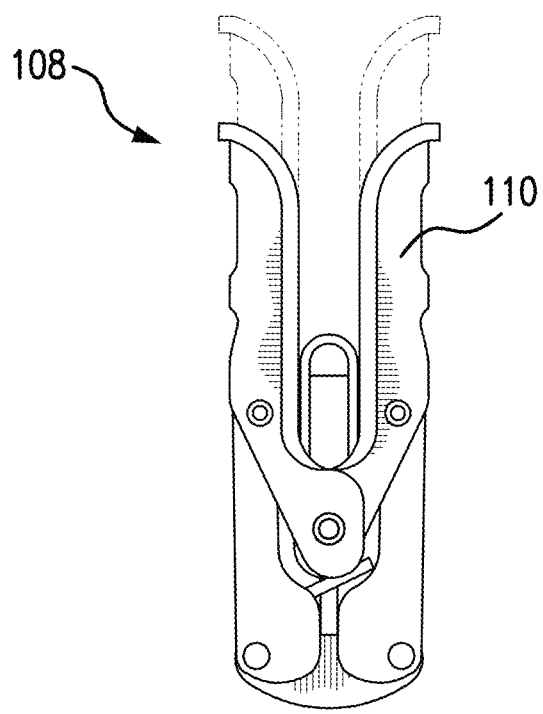
FIGS. 2A-2C are side views of the fixation device of FIG. 1 at various positions, wherein optional arms of greater length are depicted with dashed lines.
Figure 2B:
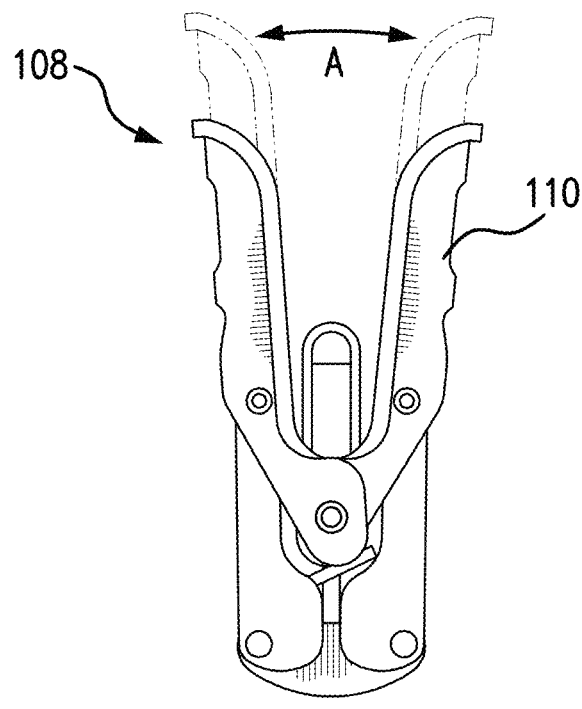
Figure 2C:
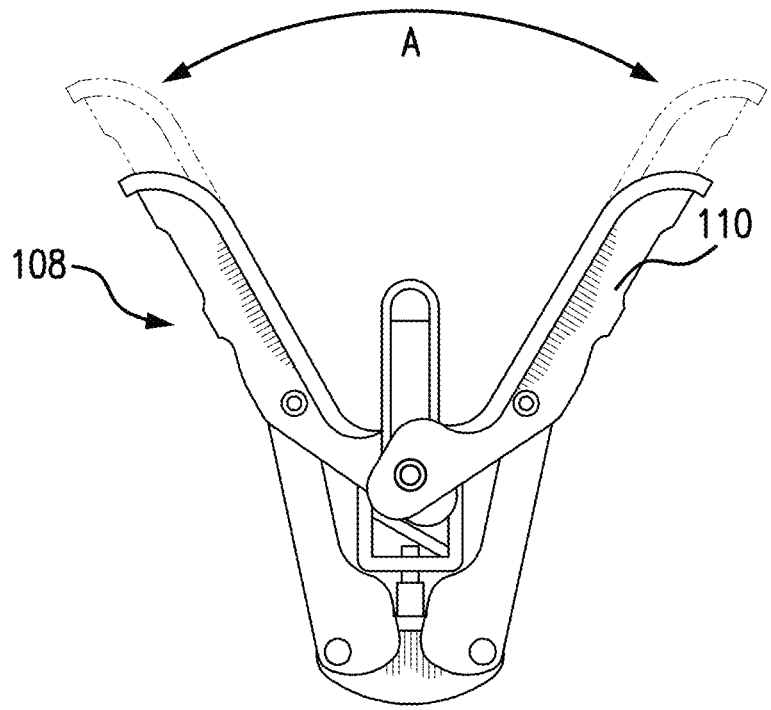

As depicted herein in FIGS. 2A-2C, various positions of the fixation device 104 are depicted for purpose of illustration and not limitation. Arms of longer length are illustrated in dashed lines for comparison to shorter arms. In FIG. 2A, the fixation device arms are positioned axially in alignment, e.g., vertically, or nearly vertically as shown. FIGS. 2B and 2C illustrate the arms positioned with an angle A between each other. In FIG. 2B, angle A is about 10 degrees and in FIG. 2C angle A is about 60 degrees. As disclosed herein, the fixation device is in the closed position when angle A is about 30 degrees or less, although another angle may result when leaflets of greater thickness are captured therebetween. Although not depicted, the arms can continue to open after angle A exceeds 180 degrees, e.g., inverted.

In accordance with the disclosed subject matter, the fixation device 104 further includes at least one gripping element 116, 118 moveable relative to the at least one arm 108, 110 to capture a native leaflet therebetween. Gripping elements 116, 118 are shown, for example, in FIG. 1. The at least one gripping element 116, 118 can be moveable relative to the at least one arm 108, 110 to capture a second native leaflet therebetween. In particular, the at least one gripping element 116, 118 has a first end 228 coupled to a portion of the fixation device and a free end 230 moveable relative to the at least one arm 108, 110. The at least one gripping element 116, 118 has a mid-length portion disposed between the first end 228 and the second end 230. As embodied herein, each gripping element can include a plurality of friction elements 152, in some cases, positioned in rows. For example, each gripping element 116, 118 can have at least four rows of friction elements 152. The friction elements 152 can allow for improved tissue engagement during leaflet capture. If the fixation device requires adjustment after an initial leaflet capture, the arms can be opened, the gripping element can be raised vertically, and tissue can disengage from the fixation device, facilitating re-capture.

For example, and with reference again to FIG. 1, each gripping element 116, 118 can be biased toward each respective arm 108, 110. Prior to leaflet capture, each gripping element 116, 118 can be moved inwardly toward a longitudinal center of the device (i.e., away from each respective arm 108, 110) and held with the aid of one or more gripping element lines (not shown) which can be in the form of sutures, wires, rods, cables, polymeric lines, or other suitable structures. The gripping line elements can be operatively connected with the gripping elements 116, 118 in a variety of ways, such as by being threaded through loops (not shown) disposed on the gripping elements 116, 118.

Figure 3:
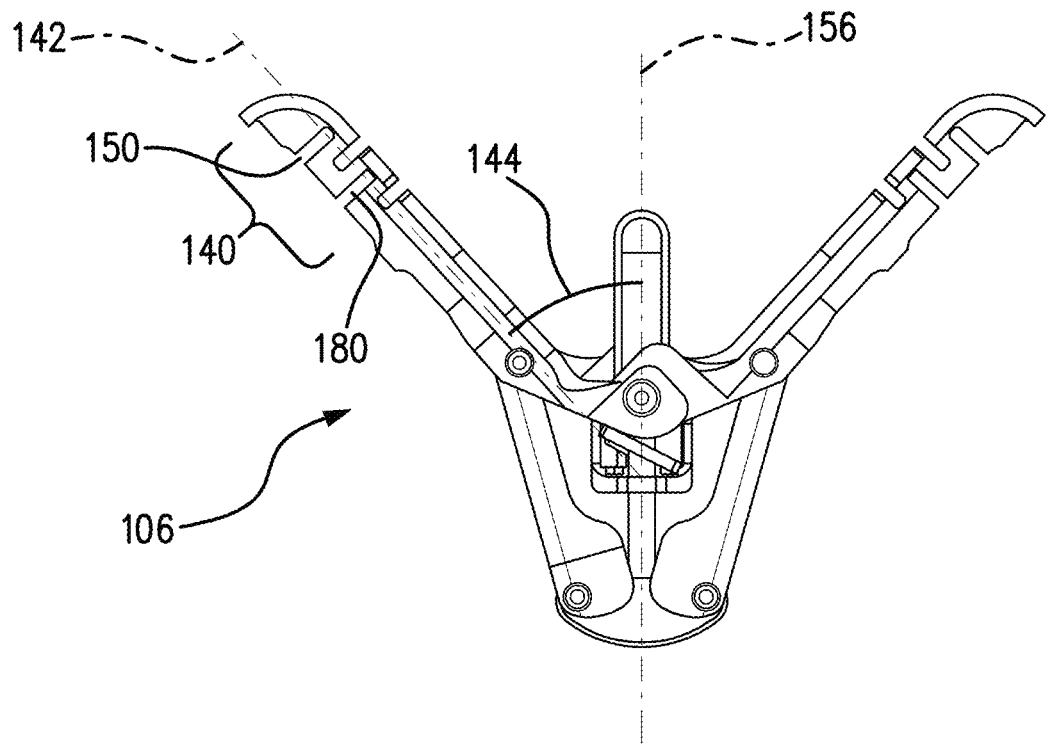
FIG. 3 is a side view of an alternative embodiment of a fixation device having arms with flexure portions in an undeformed condition.
Figure 14A:
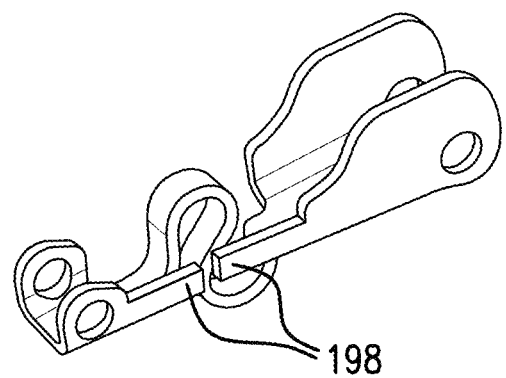
FIG. 14A is a perspective view of a flexure portion including stops.
Figure 14B:
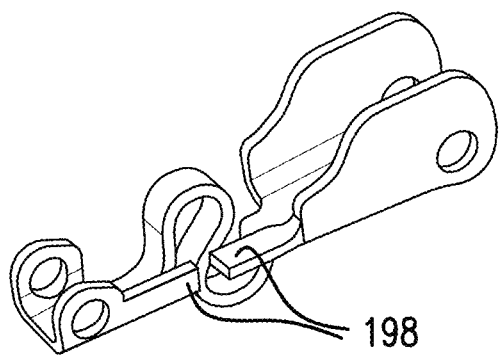
FIG. 14B is a perspective view of the flexure portion of FIG. 14A including stops in an alternative orientation.
Figure 15:
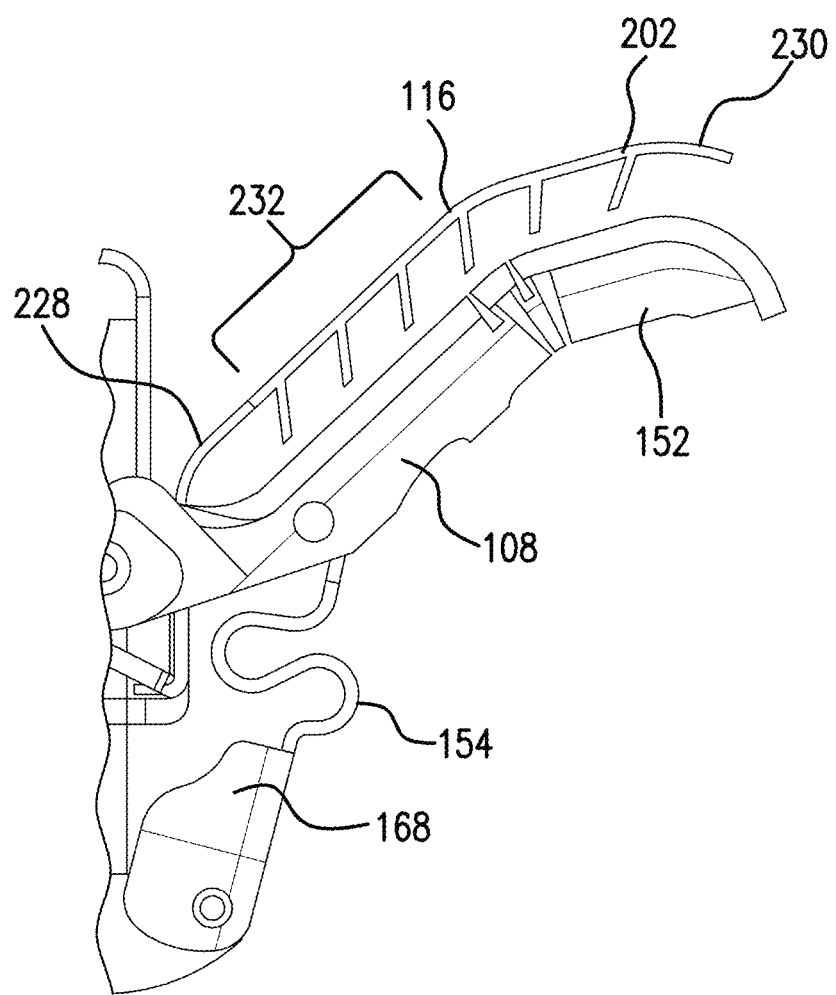
FIG. 15 is a side view of a portion of an alternative embodiment of a fixation device having multiple flexure portions and a gripping element with a biased end.

In accordance with the disclosed subject matter, and with reference to the embodiments disclosed in FIGS. 3-11, for purpose of illustration and not limitation, the arms can have a contact portion 140 that is capable of flexing. Referring to FIG. 3, the at least one arm 108, 110 includes the contact portion 140 configured to engage native heart valve tissue, the contact portion 140 defining a contact portion axis 142. A distal portion 106 of the fixation device includes a flexure portion 150 configured, with the arm in a selected position, to enable the contact portion 140 to move within a flex angle range between an undeformed contact portion angle 144 relative to the central axis 156 and a flexed contact portion angle 146 relative to the central axis 156. As embodied herein, the flexed contact portion angle 146 is greater than the undeformed contact portion angle 144. Further, the flex angle range is about 10 degrees up to about 45 degrees. The flexure portion 150 can be included on the at least one arm 108, as depicted in FIGS. 3-7, on the at least one leg 168, 169, as depicted in FIGS. 8-14, or on both the arm and the leg, as depicted in FIG. 15. As described in detail below, when the flexure portion is included on both the arm and the leg, the flex at the arm combines with the flex at the leg to enable the overall flex angle range at the contact portion 140.

Figure 4:
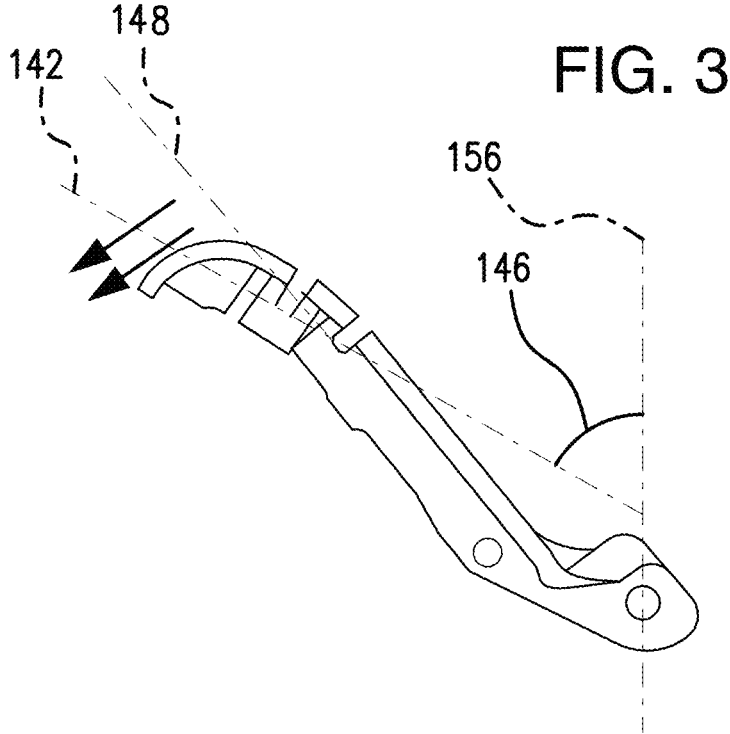
FIG. 4 is a side view of one of the arms of FIG. 3 with the flexure portion in a deformed condition.
Figure 5A:
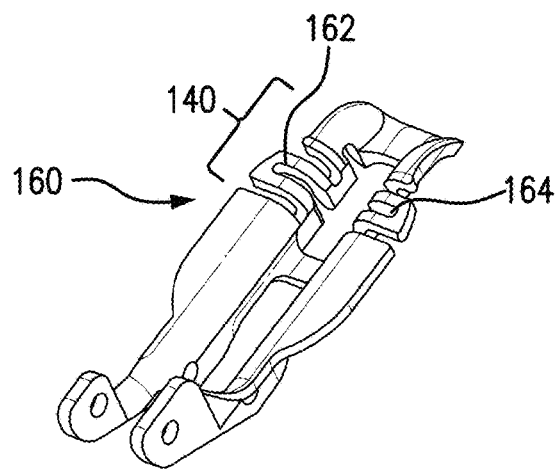
FIGS. 5A-5C illustrate a perspective view, a back view, and a side view, respectively, of one of the arms of FIG. 3.
Figure 5B:
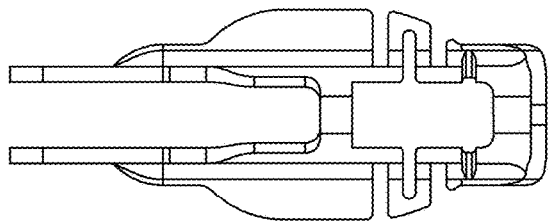
Figure 5C:
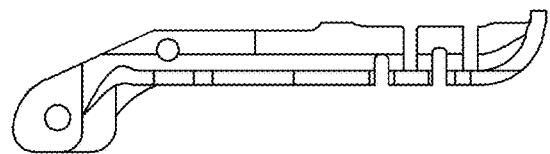

As further embodied herein in FIGS. 3-7, and in accordance with the disclosed subject matter, the at least one arm 108, 110 can include the flexure portion 150. The at least one arm 108, 110 can also include a deformable frame 160 comprising the flexure portion 150 and having first and second deformable portions 162, 164. Each of the first and second deformable portions 162, 164 can be disposed along a respective lateral side of the deformable frame 160. Furthermore, each of the first and second deformable portions 162, 164 can have an undeformed condition wherein the contact portion 140 is at the undeformed contact portion angle 144 and a deformed condition wherein the contact portion 140 is at the flexed contact portion angle 146. For purpose of illustration and not limitation, the undeformed condition is shown in FIGS. 3 and 5 and the deformed condition is shown in FIG. 4. The flexure portion 150 can include at least one slit 180 configured to enable the contact portion 140 to move within the flex angle range as previously defined between the undeformed contact portion angle 144 and the flexed contact portion angle 146. As recognized by one of skill of the art, when the flexure portion is only included on the arm, the flex angle range can also be defined by the range of enabled flexion, when the arm is at a selected position, between the contact portion axis 142 and the arm midsection axis 148, as illustrated in FIG. 4.

In accordance with another aspect of the disclosed subject matter, the at least one slit 180 can include at least one transverse cut in opposing lateral sides of the at least one arm 108, 110. Further, the at least one slit 180 can include a plurality of transverse cuts extending from each opposing lateral side of the at least one arm 108, 110. The at least one slit 180 can be comprised of side cuts and/or top down cuts. Each of the at least one slit 180 can be between about 0.01 inch to about 0.05 inch wide. Further, the width of each of the at least one slit 180 can be about 60 percent to about 200 percent the thickness of the arm. Each slit can provide about 5-15 degrees of flexion to the flex angle range, such the flex angle range can be about 5-15 degrees for a single slit, about 10-30 degrees for two slits, and about 15-45 degrees for 3 slits.

The at least one arm 108, 110 can extend from a first end proximate the central element 174 to an opposing second end, wherein the contact portion 140 can be proximate the opposing second end, and the flexure portion 150 can be adjacent the contact portion 140. Additionally, each of the at least one slit 180 can be filled with a polymer having a durometer less than a durometer of the at least one arm 108, 110. The polymer can be configured to limit the flexed contact portion angle. The polymer can also cover rough surfaces and edges. In accordance with another aspect of the disclosed subject matter, the at least one slit 180 can further encourage cellular overgrowth on the at least one arm 108, 110, and can be used in combination with a textile material cover for this purpose.

Furthermore, the at least one slit 180 can be formed of a kerf cut. A kerf cut can be a minimum width slit cut created by a given manufacturing method, for instance a laser spot size or a cutting blade width. A kerf cut can be one or more cuts in a material in a selected geometry that increases the flexibility of the material in a desired manner. The cuts can be made in a number of different geometries. For example, the cuts can be configured parallel to each other. Additionally or alternatively, the cuts can be configured perpendicular to each other, or at any other desired angle. The cuts can be straight or curved and can be uniform or non-uniform thicknesses. In this manner, the characteristics of the cuts be selected to obtain an overall desired flexibility in the flexure portion 150.

Figure 6:
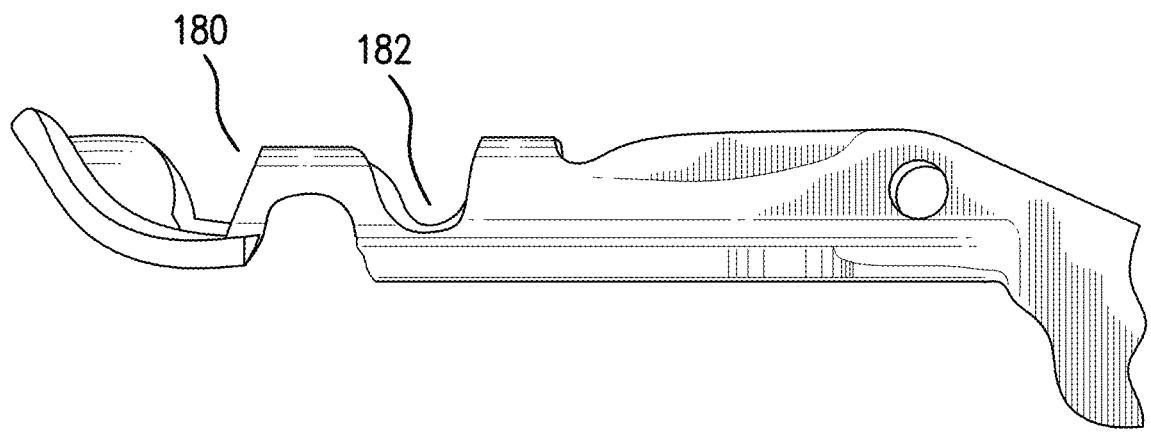
FIG. 6 is a side view of another embodiment of an arm having a flexure portion with radiused cuts.

As shown in FIG. 4, the flexure portion 150 can be configured for portions of each deformable frame to contact each other during a maximum desired deformation. As such, self-contact between portions of the flexure portion 150 can limit the flexed contact portion angle 146 and create a continuous radius of curvature throughout the flexure portion. Additionally, and as shown in FIG. 6, the at least one slit 180 can comprise a radiused cut 182 to distribute stresses more evenly within the flexure portion 150.

Figure 7A:
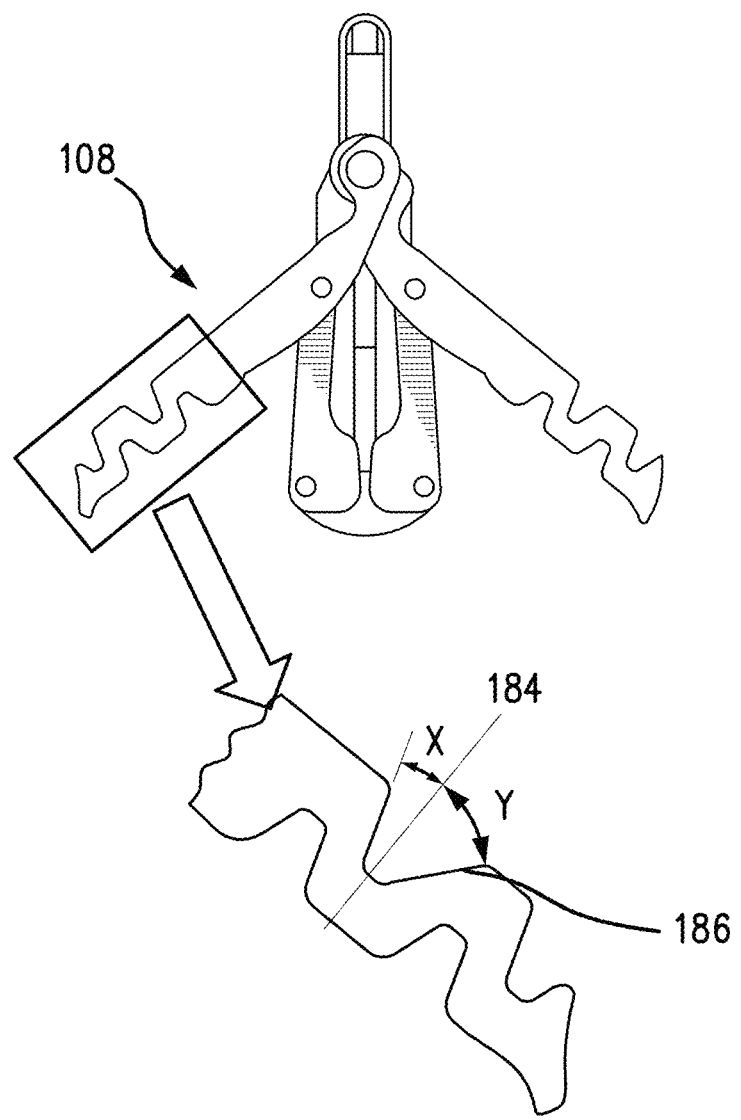
FIG. 7A is a side view of a fixation device in an inverted position comprising an enlarged schematic illustrating a further alternative embodiment of flexure portion.
Figure 7B:
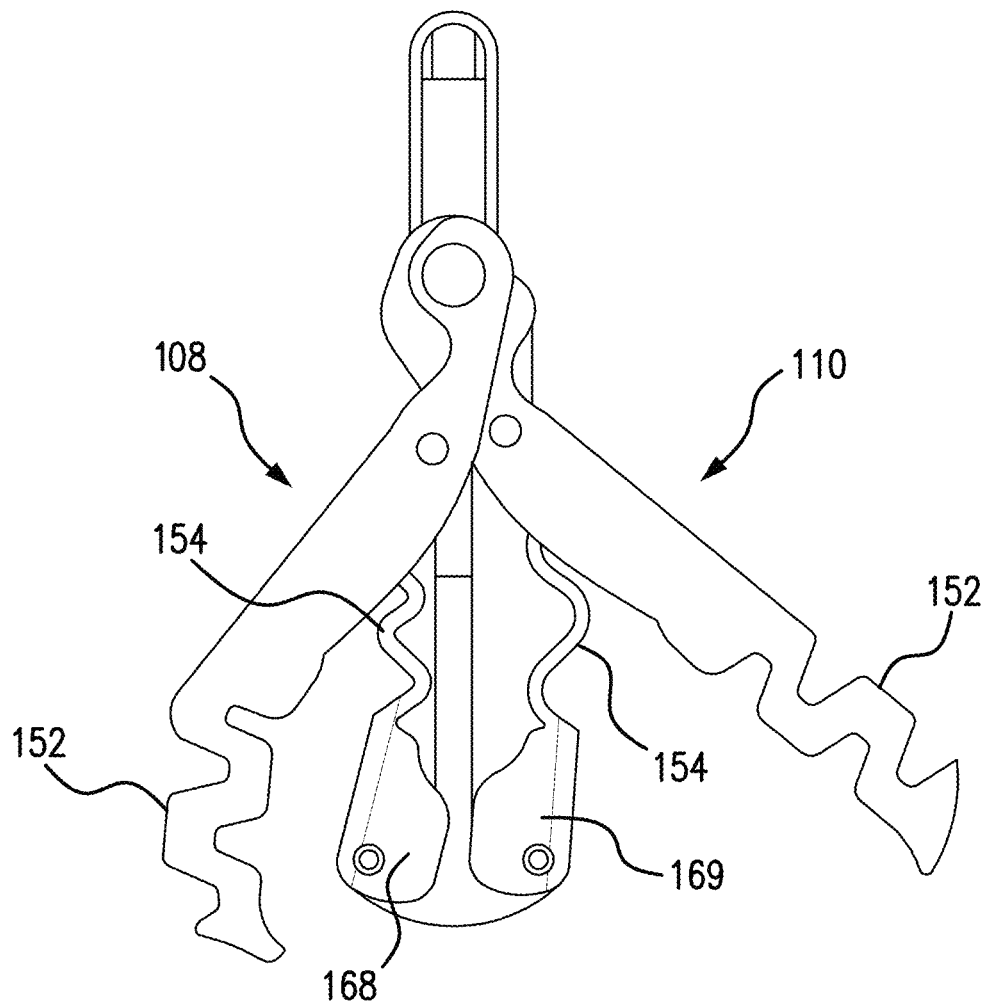
FIG. 7B is a side view of an alternative embodiment of a fixation device in an inverted position having multiple flexure portions.
Figure 8:
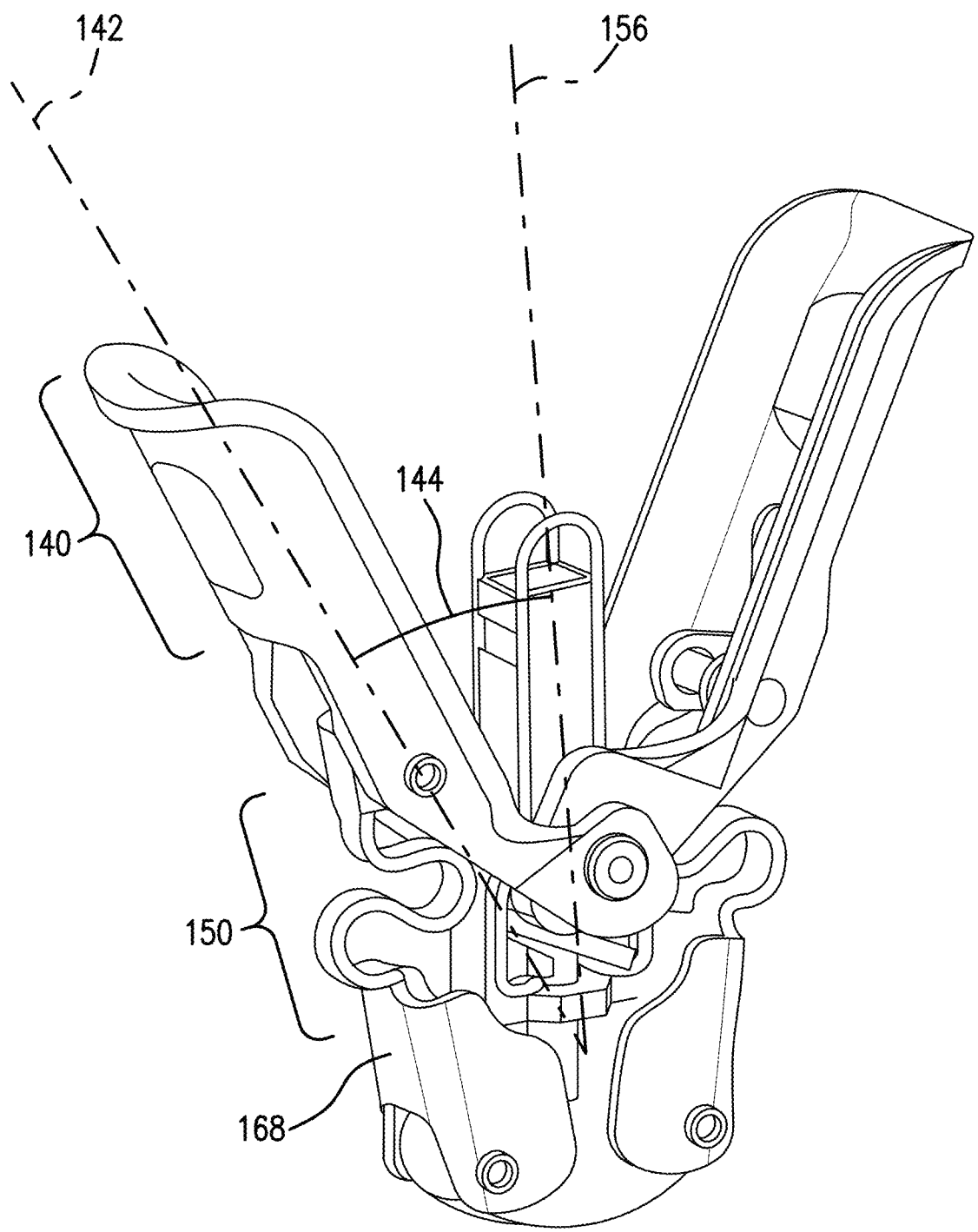
FIG. 8 is a perspective view of an alternative embodiment of a fixation device having legs with flexure portions.
Figure 9A:
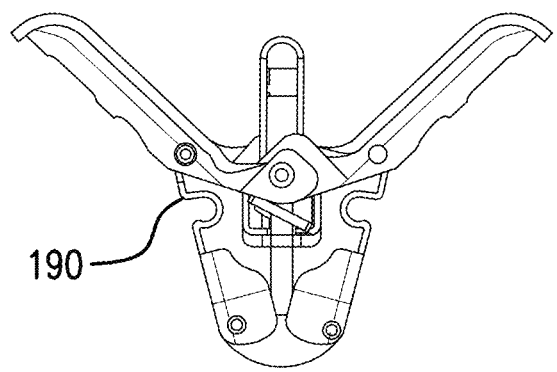
FIG. 9A is a side view of another embodiment of a fixation device having flexure portions comprising a C-shaped compression link.
Figure 9B:
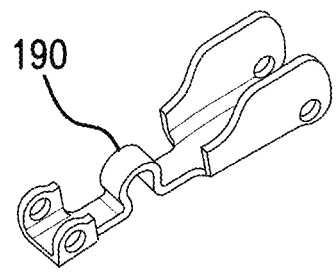
FIG. 9B is a perspective view of the C-shaped compression link of FIG. 9A.
Figure 10A:
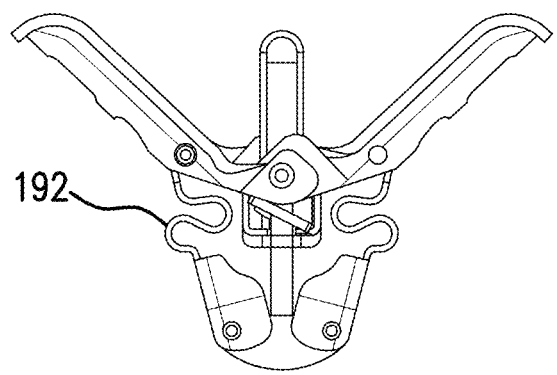
FIG. 10A is a side view of an exemplary embodiment of a fixation device having flexure portions comprising an S-shaped compression link.
Figure 10B:
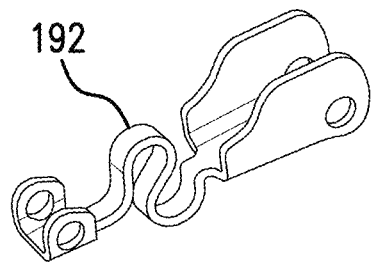
FIG. 10B is a perspective view of the S-shaped compression link of FIG. 10A.
Figure 11A:
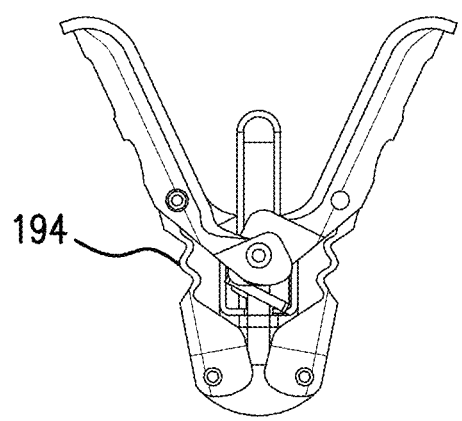
FIG. 11A is a side view of another embodiment of a fixation device having flexure portions comprising a Z-shaped compression link.
Figure 11B:
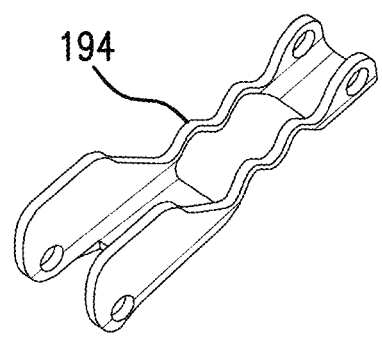
FIG. 11B is a perspective view of the Z-shaped compression link of FIG. 11A.

As further embodied herein in FIG. 7A-B, the fixation device can be configured in an inverted position. In FIG. 7A, the at least one slit 180 can include a cut having a wider angle on one side of the cut to enable tissue to more freely release from the cut. For example, a cut having a wide angle on an outer side of the cut can enable the fixation device 104 to retract through a valve in an inverted position with a smoother surface on a trailing side 186 of the cut. This can reduce the potential for tissue catching on the trailing side 186. In particular, and as shown in the expanded portion of FIG. 7A for purpose of illustration and not limitation, a cut can have reference axis 184 extending perpendicularly from an apex of the cut. An inner side of the cut can have side wall with an angle X relative the reference axis 184. Likewise, an outer side of the cut can have a side wall with an angle Y relative the reference axis 184. As disclosed herein, angle X can be about 30 to 45 degrees and angle Y can be about 60 to about 80 degrees.

In FIG. 7B, and in accordance with another aspect of the disclosed subject matter, the flexure portion can include an arm flexure portions 152 disposed on the arms 108, 110 and configured to enable an arm source flexion range. The flexure portion can further include leg flexure portions 154 disposed on the legs 168, 169 and configured to enable a leg source flexion range. The inverted position of the fixation device, as shown, can be used to facilitate withdrawal of the device from the ventricle to the atrium by avoiding interactions with heart anatomy or reducing resistance from the heart anatomy, including leaflets and chordae. To further reduce resistance, the fixation device can be flexed at the flexure portion to a narrower profile. For example, and as shown in FIG. 7B for purpose of illustration and not limitation, the first arm 108 can be under resistance from heart anatomy, such as from chordae catching and resting the end of the arm 108 during a withdrawal procedure. The leg flexure portion 152 on the corresponding leg 169, or arm flexure portion 154 on the corresponding arm 108, or both (as shown in FIG. 7B) can flex to narrow the overall profile of the fixation device and reduce resistance caused by the heart anatomy. As shown, and as a result of resistance on the first arm 108, the leg flexure portion 154 of the first leg 168 is flexed as compared to the leg flexure portion 154 of the second leg 169. As a result, the first arm 108 is flexed downward to a narrower configuration and second arm 110 is not flexed. Likewise, the arm flexure portion 152 of the first arm 108 is flexed as compared to the arm flexure portion 152 of the second arm 110. As a result, the end of the arm 108 is flexed inward to narrower configuration, and end of the arm 110 is not flexed. Moreover, it is understood that a device having only a leg flexure portion 152 or only an arm flexure portion 154 can likewise flex on their own to narrow the fixation device profile in the inverted position. Furthermore, it is contemplated that any leg flexure portion 152 and any arm flexure portion 154 in the disclosed subject matter herein can be incorporated in the fixation device shown in FIG. 7B and function in a substantially similar manner.

During manufacturing, the at least one slit 180 can be formed from any number of different processes and techniques. For example, the at least one slit 180 can be a 3D printed direct metal laser sintered (DMLS) part made from steel, cobalt chrome, titanium, nitinol, other alloys, or 3D printed plastics. Additionally or alternatively, the at least one slit can be metal stamped with cutaways, pierced, etched, laser cut, or electrical discharge machined. Cut depth and fillet radii may be adjusted using electro-chemical treatment such as electro-polishing. Each cut within the at least one slit 180 can have a width that is at least one and a half times a thickness of the flexure portion. For example, the flexure portion thickness can be about 0.03 inch and the cut width can be about 0.05 inch. Furthermore, the flexure portion 150 and portions of the arm 108 proximate the flexure portion 150 can have a varied material thickness. A varied material thickness can improve flexibility and stress distribution at both the flexure portion 150 and along portions of the arm 108 proximate the flexure portion 150.

Figure 12:
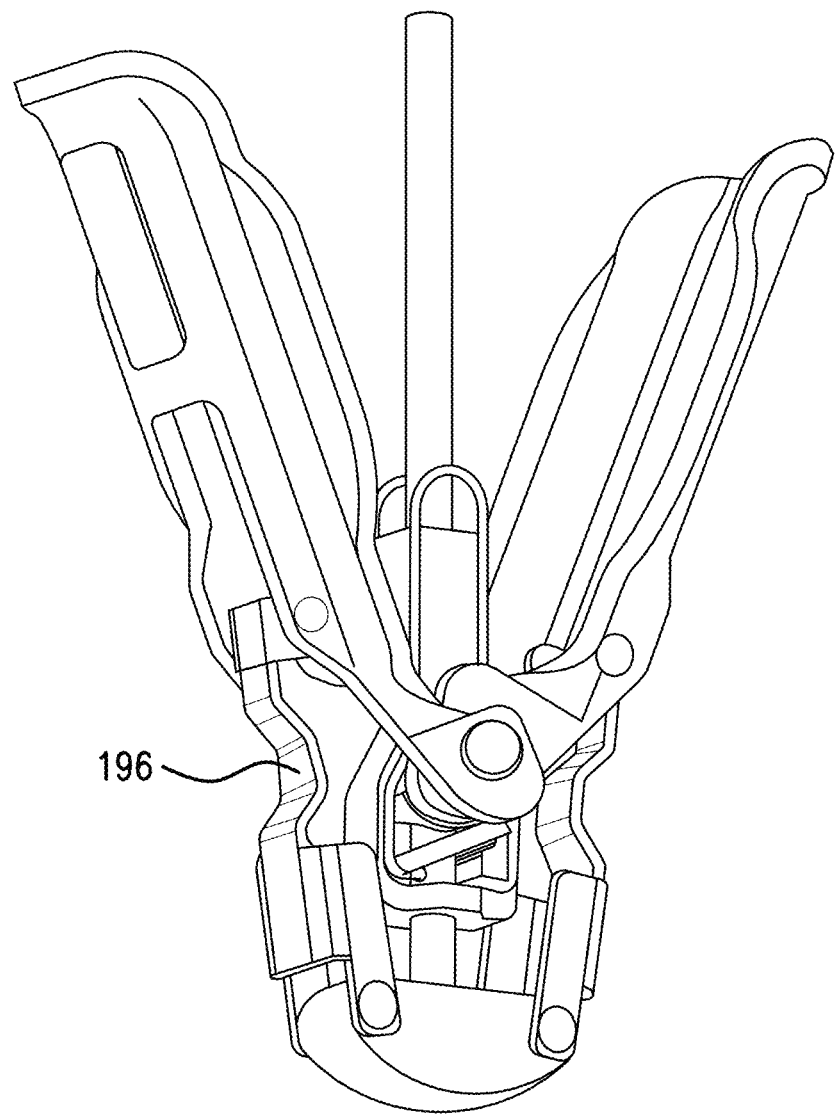
FIG. 12 is a perspective view of an alternative embodiment of a fixation device having a trapezoidal-shaped compression link.
Figure 13A:
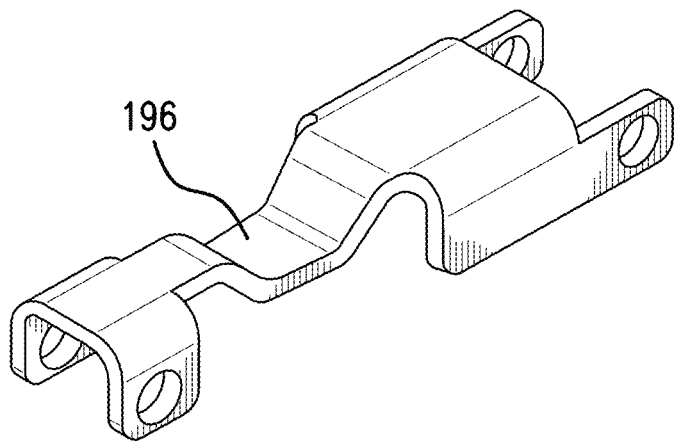
FIG. 13A is a perspective view of the trapezoidal-shaped compression link of FIG. 12.
Figure 13B:
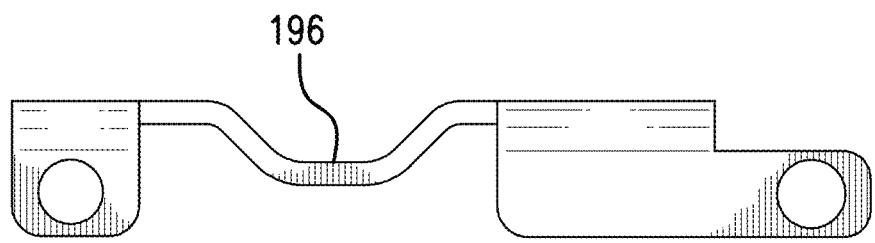
FIG. 13B is a side view of the trapezoidal-shaped compression link of FIG. 12.
Figure 13C:
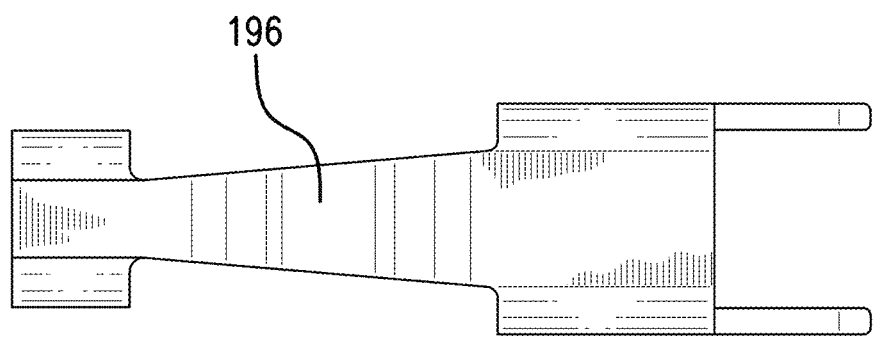
FIG. 13C is a front view of the trapezoidal-shaped compression link of FIG. 12.

Turing now to FIGS. 8-14, and in accordance with another aspect of the disclosed subject matter, the at least one leg 168, 169 can include the flexure portion 150. The flexure portion 150 in the at least one leg 168, 169 can include a spring feature configured to deform elastically under a compressive load. The flexure portion 150 spring feature can be formed of any number of different configurations. For example, the flexure portion 150 can include a C-shaped compression link 190 configured to enable the flex angle range be about 10 to about 20 degrees, as shown in FIGS. 9A and 9B. For further flexibility, the flexure portion 150 can include an S-shaped compression link 192 configured to enable the flex angle range be about 20 to about 40 degrees, as shown in FIGS. 10A and 10B. Alternatively, the flexure portion 150 can include a Z-shaped compression link 194 configured to enable the flex angle range be about 5 degrees to 15 degrees, as shown in FIGS. 11A and 11B. As a still further alternative, the flexure portion 150 can include a trapezoidal-shaped compression link 196 configured to enable the flex angle range be about 5 to 15 degrees, as shown in FIGS. 12-13C. The trapezoidal-shaped compression link 196 can have a width dimension that increases from a proximal location to a distal location, as shown at least in FIG. 13C. This trapezoidal design provides the benefit of improved stability and fatigue resistance and provides a stable closing state wherein the trapezoidal-shaped compression link 196 can contact a central portion of the fixation device when the arm 108 is in a closed position. All embodiments shown in FIGS. 9A, 9B, 10A, 10B, 11A, 11B, 12, 13A, 13B, and 13C may be configured with concave or convex curvature orientations.

Bends in the link members can be configured to touch each other to limit the maximum amount of compression, and thus, can limit the flex angle range. In accordance with another embodiment, and with reference to FIGS. 14A and 14B, the flexure portion 150 can include at least one stop 198 configured to limit the flex angle range. For example, the at least one stop can limit the flex angle range to up to about 10 degrees. The at least one stop 198 can be included with any flexure portion design and is not limited to the compression link shown in FIG. 14, which is for purpose of illustration and not limitation. As shown in FIG. 14, two stops 198 can be used wherein the stops 198 are configured to contact each other during flexion to limit the flex angle range. Furthermore, and turning to FIG. 14B, the stops 198 can be oriented at differing angles to each other. For example, the stops can be oriented perpendicularly, as shown herein, wherein one stop is twisted 90 degrees relative to the other stop. Differing angle orientations between the stops 198 can increase their ability to make contact with each other and avoid sliding past each other. The at least one stop disclosed herein can be configured to limit the flex angle range before another mechanism would otherwise limit the flex angle range (e.g., from the stiffness of the flexure portion or link members that touch).

During manufacturing, the leg 168, 169 including a flexure portion 150 (e.g., links 190, 192, and 194) can be 3D printed direct metal laser sintered (DMLS). The leg 168, 169 can be made of steel, cobalt chrome, titanium, other alloys, 3D printed plastics, machined, stamped, laser-cut in metal, or laser-cut in plastic. A Nitinol material can be used provide fatigue resistance and super-elasticity. Section of the leg 168, 169 can also made by a kerf cut or shaped by metal stamping, forming, or made with computer numerical control (CNC), electrical discharge machining, or other machining operations. The leg 168, 169 can include one or more of the following characteristics to obtain desired flexibility: varying material thickness, varying sizes and number of bend portions, varying material width, varying material properties (e.g., heat treatment regions of material), and varying materials. The leg 168, 169 can be constructed of any medical grade metal such as cobalt chrome, stainless steel, titanium, nickel titanium (nitinol), Elgiloy®, or medical grade polymers such as poly-lactic acid (PLA), polyethylene, ABS, polyurethane, PEEK, or other similar materials or combinations thereof.

Turing now to FIG. 15, and in accordance with another aspect of the disclosed subject matter, the at least one gripping element 116 includes a mid-length portion 232 disposed along the at least one gripping element 116 and spaced from a free end 230 of the at least one gripping element. The at least one gripping element 116 further comprises an end portion 202 proximate the free end 230, wherein the end portion 202 is biased towards the at least one arm 108 relative to the mid-length portion 232. The end portion 202 can enable the tip of the gripping element 116 to maintain a force towards a corresponding arm contact portion 140 during flexion of the contact portion. The end portion 202 bias can be formed using similar manufacturing techniques as the techniques used to form other biases in the gripping element 116. A bend formed between the end portion 202 and the mid-length portion 232 can create the bias.

With continued reference to FIG. 15, the flexure portion 150 can include an arm flexure portion 152 disposed on the at least one arm 108 configured to enable an arm source flexion range, and the flexure portion 150 further includes a leg flexure portion 154 disposed on the at least one leg 168, 169 and configured to enable a leg source flexion range. The arm source flexion range and leg source flexion range combine to enable the flex angle range. The combined arm source flex angle range and leg source flex angle range is about 45 degrees or less. For example, an arm source flexion range of about 30 degrees combined with a leg source flexion range of about 15 degrees results in the flex angle range being about 45 degrees. The leg flexure portion 154, when flexed, creates global flex along an entire length of the arm 108. The arm flexure portion, when flexed, creates a localized flex at the contact portion 140, rather than the entire length of the arm 108.

Figure 16:
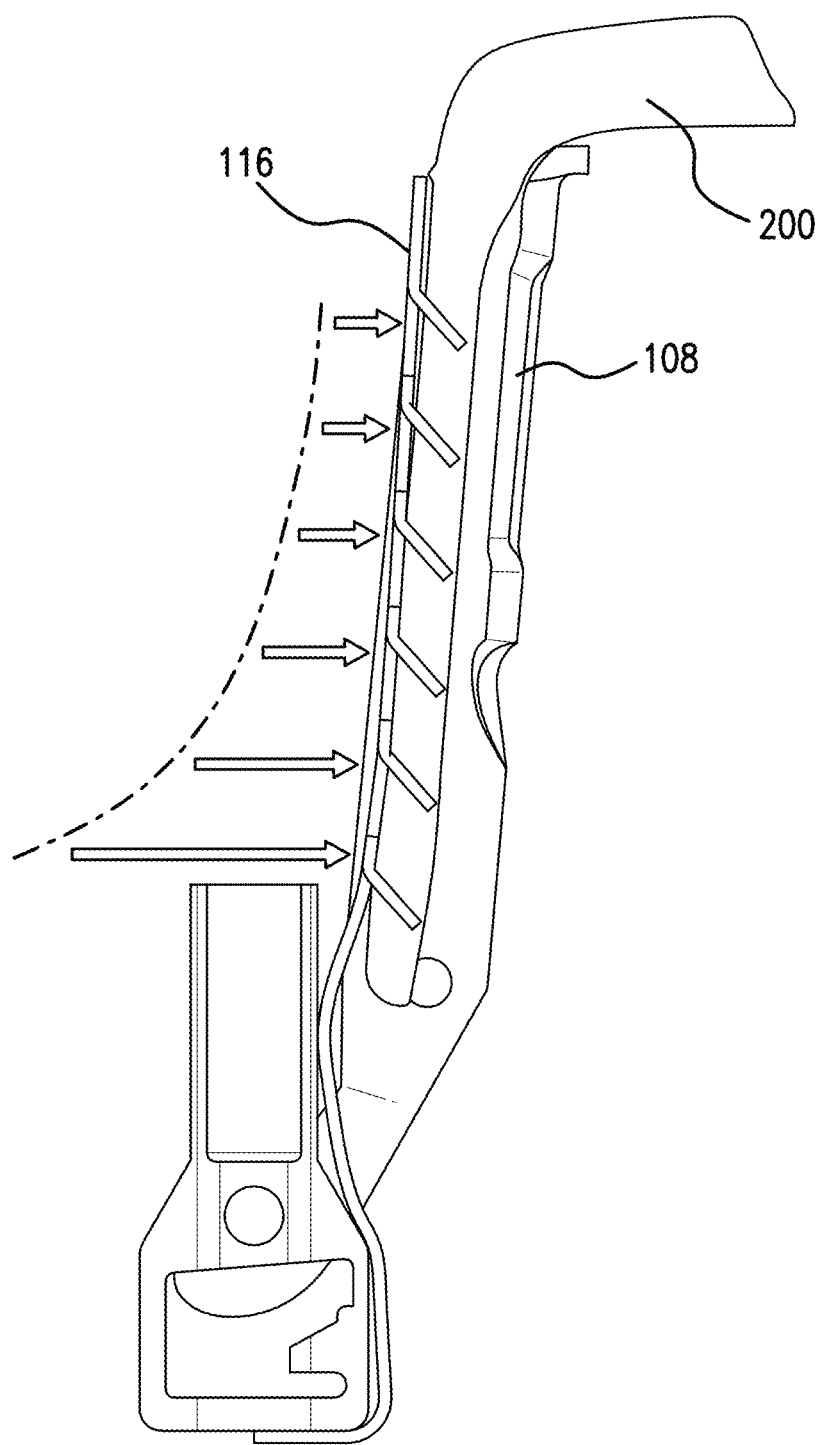
FIG. 16 is a side view of a gripping element, native leaflet, and arm illustrating relative grasping forces along the length of the gripping element.

Turning now to FIG. 16, and in accordance with another aspect of the disclosed subject matter, a gripping element 116 and an arm 108 are illustrated with a native leaflet 200 grasped therebetween. As depicted, for purpose of illustration and not limitation, arrows are shown to indicate a relative amount of force produced by the biased gripping element 116 against the leaflet and the arm 108. As shown, the relative force decreases towards the free end of the gripping element 116. The force corresponds to the grasp force placed on a native leaflet 200, so, the greatest amount of grasp force on a native leaflet is spaced from the contact portion 140. Accordingly, a fixation device can be configured to limit global flexure along an entire length of the arm 108 as compared to a flex at the contact portion 140. Reduced flex along the length of the arm 108 (e.g., up to about 30 degrees) can ensure a secure leaflet grasp, while an increased flex at the contact portion (e.g., up to 45 degrees) can reduce strain on a native leaflet 200.

The embodiments illustrated herein are adapted for repair of a heart valve, such as a mitral valve, using an antegrade approach from a patient's left atrium. Prior to a procedure, imaging and various tests can be performed to anticipate and diagnose a patient's individual circumstances and assist a physician in selecting a fixation device having the desired parameters.

While the embodiments disclosed herein utilize a push-to-open, pull-to-close mechanism for opening and closing arms it should be understood that other suitable mechanisms can be used, such as a pull-to-open, push-to-close mechanism. Likewise, other actuation elements can be used for deployment of the gripping elements.

The components disclosed herein, such as the arm and leg components, can be formed with an alternative geometry by manufacturing from tubing. For example, tube cutting manufacturing techniques can be used wherein each component would have a "C" shaped cross section (e.g., a "half pipe") cut from a tube to create a trough for the arm and a profile for the leg.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A fixation device for fixation of leaflets of a heart valve comprising:
a central element defining a central axis;
a distal portion comprising:
at least one arm coupled to the central element, the at least one arm moveable to a selected position between a fully open position and a fully closed position, and
at least one leg operatively coupled to the at least one arm and configured to move the at least one arm to the selected position between the fully open position and the fully closed position,
wherein the at least one arm includes a contact portion configured to engage native heart valve tissue, the contact portion defining a contact portion axis,
wherein the distal portion includes a flexure portion configured to enable the contact portion in the selected position to move within a flex angle range between an undeformed contact portion angle relative to the central axis and a flexed contact portion angle relative to the central axis, wherein the flexed contact portion angle is greater than the undeformed contact portion angle, the flex angle range being about 10 degrees to about 45 degrees; and
at least one gripping element moveable relative to the at least one arm to capture a native leaflet therebetween.

2. The fixation device of claim 1, wherein the at least one arm comprises the flexure portion.

3. The fixation device of claim 2, wherein the at least one arm comprises a deformable frame comprising the flexure portion and having first and second deformable portions, each of the first and second deformable portions disposed along a respective lateral side of the deformable frame.

4. The fixation device of claim 3, each of the first and second deformable portions having an undeformed condition wherein the contact portion is at the undeformed contact portion angle and a deformed condition wherein the contact portion is at the flexed contact portion angle.

5. The fixation device of claim 2, wherein the flexure portion includes at least one slit configured to enable the contact portion to move between the undeformed contact portion angle and the flexed contact portion angle.

6. The fixation device of claim 5, wherein the at least one slit comprises at least one transverse cut in opposing lateral sides of the at least one arm.

7. The fixation device of claim 5, wherein the at least one slit comprises a plurality of transverse cuts extending from each opposing lateral side of the at least one arm.

8. The fixation device of claim 5, wherein each of the at least one slit is between about 0.01 inch to about 0.03 inch wide.

9. The fixation device of claim 5, wherein each of the at least one slit is filled with a polymer having a durometer less than a durometer of the at least one arm.

10. The fixation device of claim 5, wherein the at least one slit is formed of a kerf cut.

11. The fixation device of claim 2, wherein the at least one arm extends from a first end proximate the central element to an opposing second end, wherein the contact portion is proximate the opposing second end, and the flexure portion is adjacent the contact portion.

12. The fixation device of claim 2, wherein the at least one gripping element comprises a mid-length portion disposed along the at least one gripping element and spaced from a free end of the at least one gripping element, and the at least one gripping element further comprises an end portion proximate the free end, wherein the end portion is biased towards the at least one arm relative to the mid-length portion.

13. The fixation device of claim 1, wherein the at least one leg comprises the flexure portion.

14. The fixation device of claim 13, wherein the flexure portion comprises a spring feature configured to deform elastically under a compressive load.

15. The fixation device of claim 13, wherein the flexure portion comprises a C-shaped compression link configured to enable the flex angle range be up to about 15 degrees.

16. The fixation device of claim 13, wherein the flexure portion comprises an S-shaped compression link configured to enable the flex angle range be up to about 30 degrees.

17. The fixation device of claim 13, wherein the flexure portion comprises a trapezoidal-shaped compression link configured to enable the flex angle range be about 10 to 15 degrees.

18. The fixation device of claim 17, wherein the trapezoidal-shaped compression link has a width dimension that increases from a proximal location to a distal location.

19. The fixation device of claim 13, wherein the flexure portion comprises at least one stop configured to limit the flex angle range.

20. The fixation device of claim 19, wherein the at least one stop limits the flex angle range to up to about 10 degrees.

21. The fixation device of claim 1, wherein the flexure portion includes an arm flexure portion disposed on the at least one arm configured to enable an arm source flexion angle range, and the flexure portion further includes a leg flexure portion disposed on the at least one leg configured to enable a leg source flexion angle range, wherein the arm source flexion angle range and leg source flexion range combine to enable the flex angle range.

22. The fixation device of claim 21, wherein the combined arm source flex angle range and leg source flex angle range is about 45 degrees or less.

23. The fixation device of claim 1, wherein the central element comprises a base portion coupled to the at least one leg, wherein distal movement of the base portion moves the at least one leg to move the at least one arm towards the fully open position.

24. The fixation device of claim 23, wherein the fixation device is configured to prevent distal movement of the base portion when the at least one arm is in the selected position.

25. The fixation device of claim 24, wherein the fixation device further comprises a locking mechanism configured to prevent distal movement of the base portion.

\* \* \* \* \*